United States Patent
Hodorek et al.

(10) Patent No.: US 11,986,357 B2
(45) Date of Patent: May 21, 2024

(54) SURGICAL INSTRUMENT HANDLE WITH IMPLANT SIZING FEATURE AND METHOD OF USING

(71) Applicant: Synthes GmbH, Oberdorf (CH)

(72) Inventors: Brian C. Hodorek, Winona Lake, IN (US); Matt J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US)

(73) Assignee: Synthes GMBH, Oberdorf (CH)

( * ) Notice: Subject to any disclaimer, the term of this patent is extended or adjusted under 35 U.S.C. 154(b) by 319 days.

(21) Appl. No.: 17/568,904

(22) Filed: Jan. 5, 2022

(65) Prior Publication Data

US 2022/0125547 A1   Apr. 28, 2022

Related U.S. Application Data

(60) Division of application No. 16/560,923, filed on Sep. 4, 2019, now Pat. No. 11,241,293, which is a
(Continued)

(51) Int. Cl.
*A61B 90/00* (2016.01)
*A61B 17/00* (2006.01)
(Continued)

(52) U.S. Cl.
CPC .......... *A61B 90/06* (2016.02); *A61B 17/1659* (2013.01); *A61B 2017/0042* (2013.01);
(Continued)

(58) Field of Classification Search
CPC ................ A61B 90/06; A61B 17/1659; A61B 2090/035; A61B 2090/062;
(Continued)

(56) References Cited

U.S. PATENT DOCUMENTS

| 2003/0135275 A1 | 7/2003 | Garcia et al. |
| 2014/0012273 A1* | 1/2014 | Boggs .................. A61B 5/1121 606/102 |

(Continued)

FOREIGN PATENT DOCUMENTS

| EP | 3409236 A1 | 12/2018 |
| WO | 96/10962 A1 | 4/1996 |

(Continued)

OTHER PUBLICATIONS

U.S. Appl. No. 16/560,923, filed Sep. 4, 2019.
(Continued)

*Primary Examiner* — Zade Coley
*Assistant Examiner* — Diana Jones
(74) *Attorney, Agent, or Firm* — BakerHostetler

(57) ABSTRACT

A single-use handle is configured to attach to a working shaft that can support a sounder for measuring the medullary canal of a proximal radius, and a planarizer that is configured to planarize a proximal edge of the proximal radius after the proximal radius has been resected. The handle can further include a plurality of sizing cavities that are configured to receive the resected bone so as to determine the size of the resected bone. The handle can further include an ejector that is configured to decouple the planarizer from the working shaft.

10 Claims, 12 Drawing Sheets

Related U.S. Application Data continuation-in-part of application No. 16/245,191, filed on Jan. 10, 2019, now Pat. No. 11,147,542.

(60) Provisional application No. 62/638,240, filed on Mar. 4, 2018.

(51) Int. Cl.
*A61B 17/16* (2006.01)
*A61B 17/56* (2006.01)

(52) U.S. Cl.
CPC ............ *A61B 2017/00464* (2013.01); *A61B 2017/00831* (2013.01); *A61B 2017/564* (2013.01); *A61B 2090/035* (2016.02); *A61B 2090/061* (2016.02); *A61B 2090/062* (2016.02)

(58) Field of Classification Search
CPC .. A61B 2017/0042; A61B 2017/00464; A61B 2017/00831; A61B 2017/564
See application file for complete search history.

(56) References Cited

U.S. PATENT DOCUMENTS

| | | | |
|---|---|---|---|
| 2015/0066030 A1 | 3/2015 | McGinley et al. | |
| 2017/0156739 A1 | 6/2017 | Nino et al. | |
| 2018/0185166 A1* | 7/2018 | Johannaber | A61F 2/4081 |
| 2018/0257214 A1* | 9/2018 | Scheuber | B25G 3/18 |
| 2020/0100911 A1* | 4/2020 | Johannaber | A61F 2/4081 |

FOREIGN PATENT DOCUMENTS

| | | |
|---|---|---|
| WO | 2007/055441 A1 | 5/2007 |
| WO | 2018/220140 A1 | 12/2018 |
| WO | 2019/168987 A1 | 9/2019 |

OTHER PUBLICATIONS

U.S. Appl. No. 16/245,191, filed Jan. 10, 2019.
Craftmanspace, "Spaghetti Measuring Tool Plan", www.craftsmanspace.com/free-projects/spaghetti-measuring-tool-plan.html, Year 2009.
McMacken, Melissa, Types of Minimally Invasive Surgery (Robotic, Endoscopic, Laparoscopic): Johns Hopkins Medicine in Baltimore, MD, www.hopkinsmedicine.org/minimally_invasive_robotic_surgery/types.html, webpage accessed Dec. 3, 2020, 3 pages.

* cited by examiner

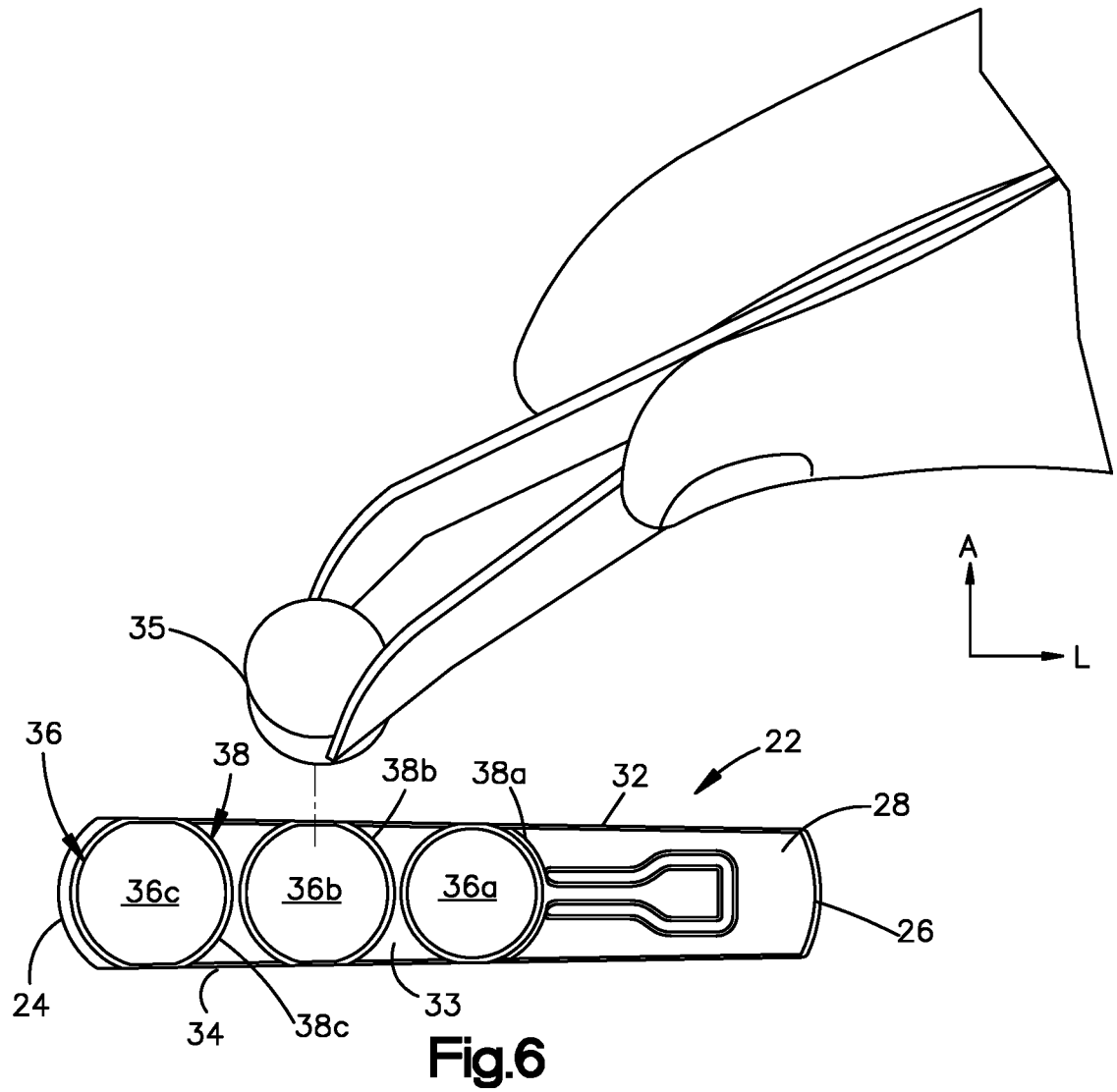
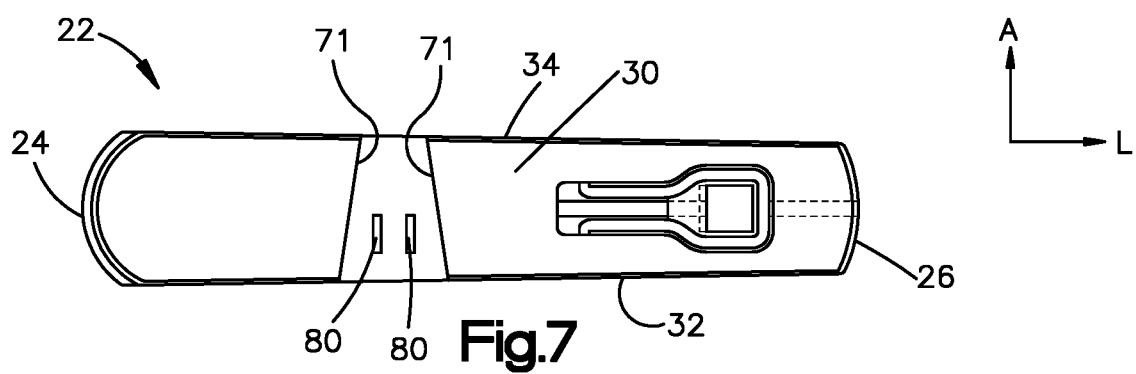

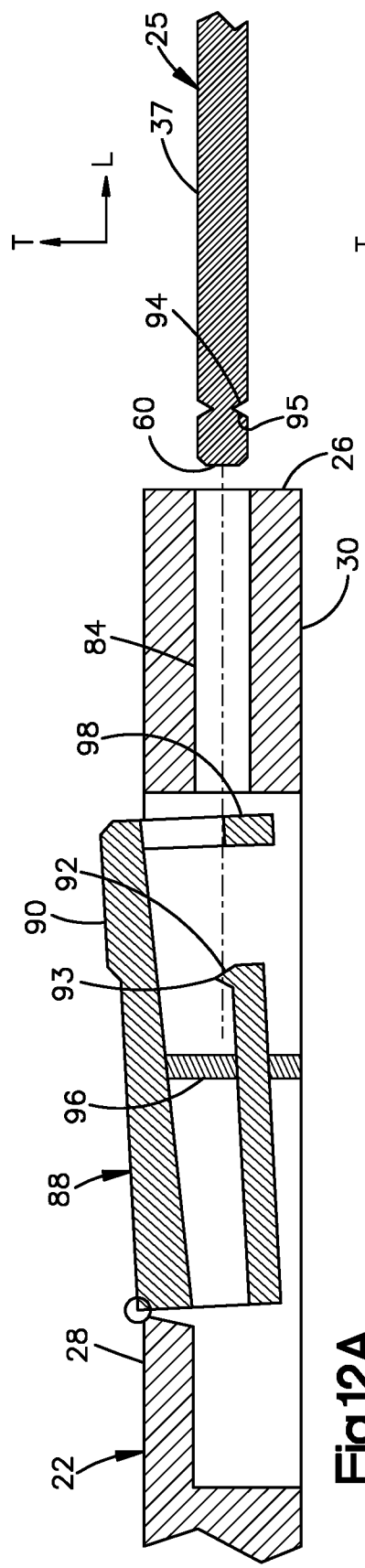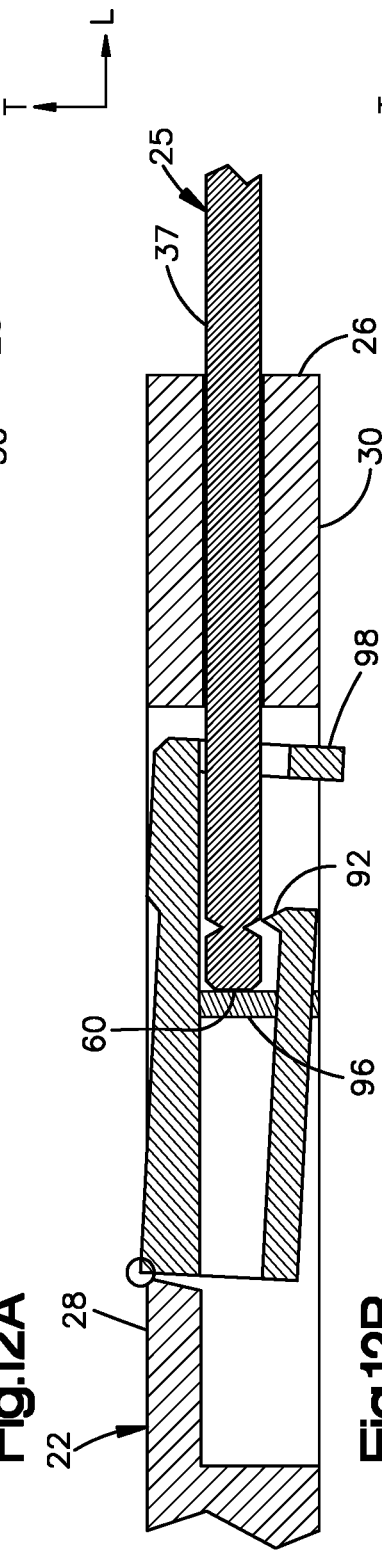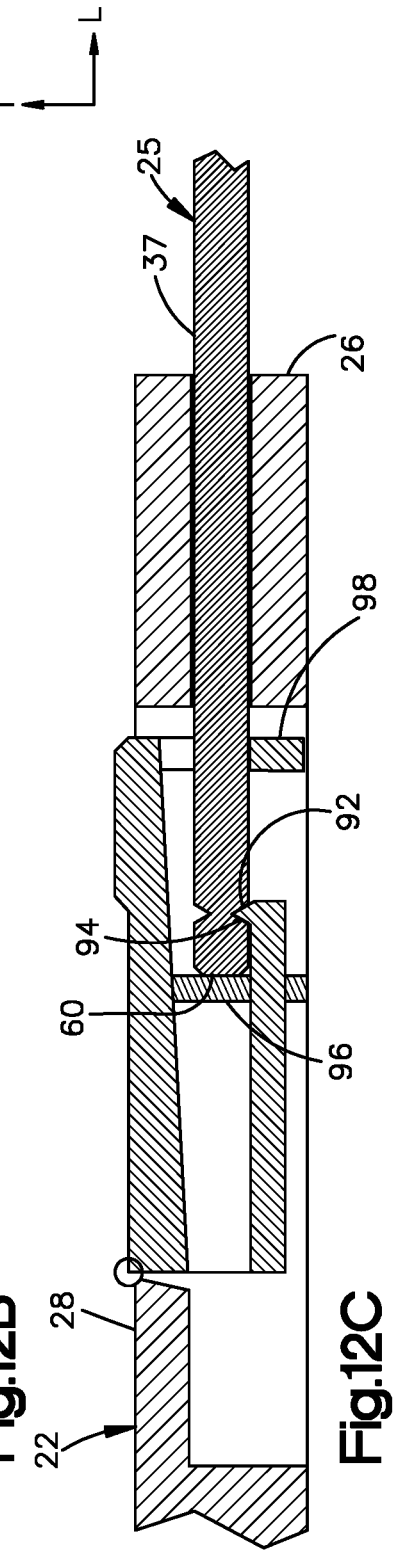
Fig.12A
Fig.12B
Fig.12C

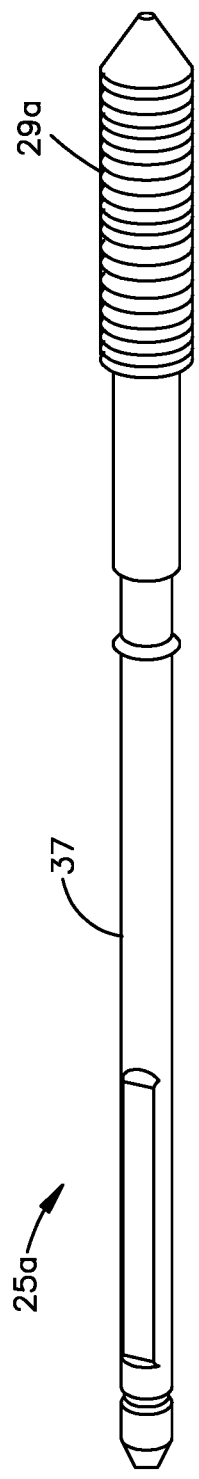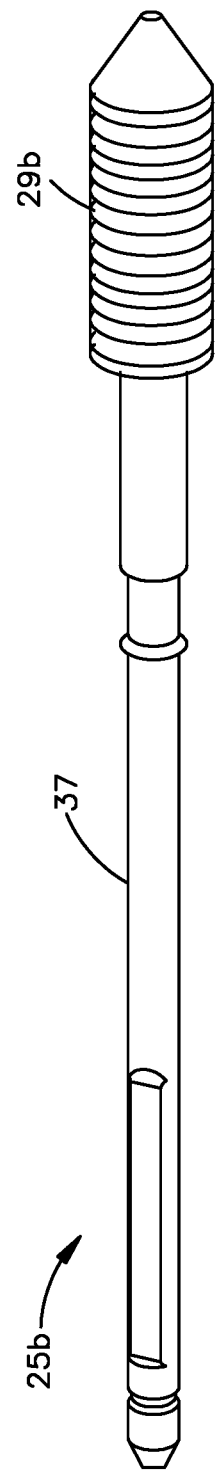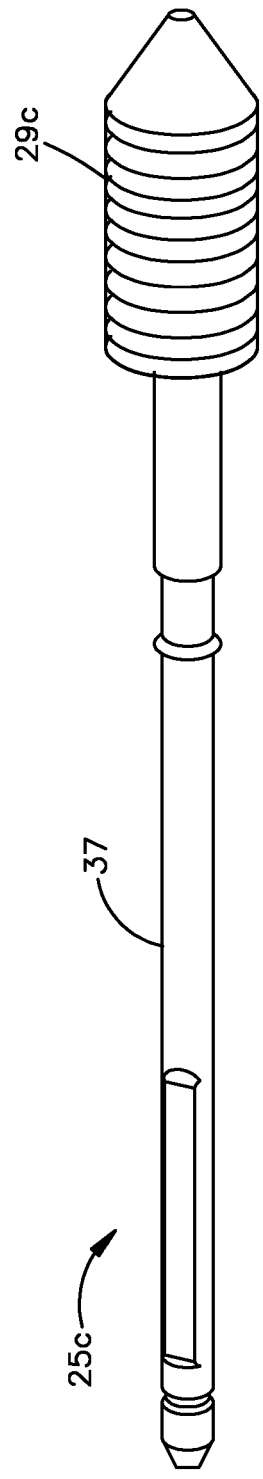

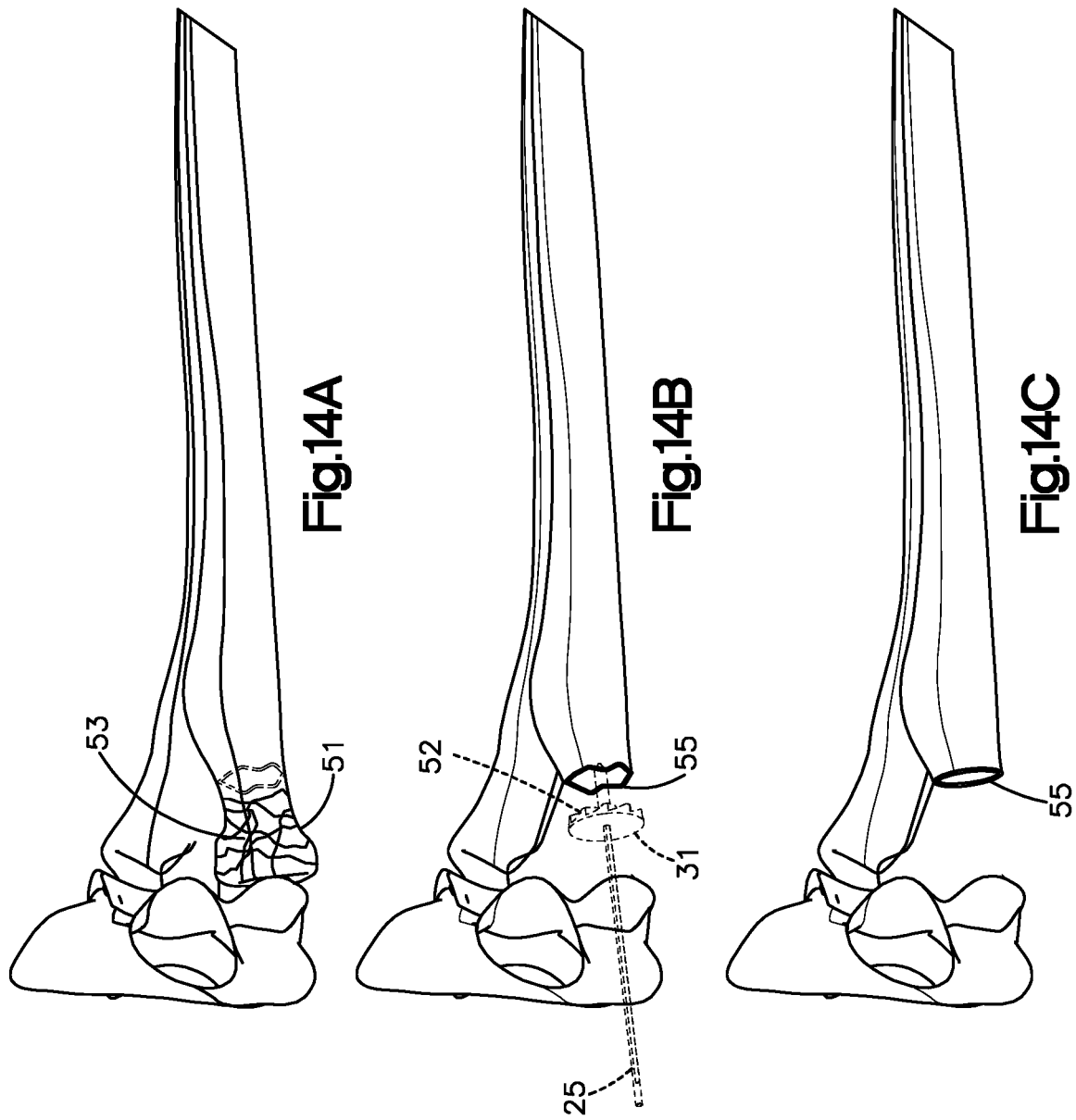

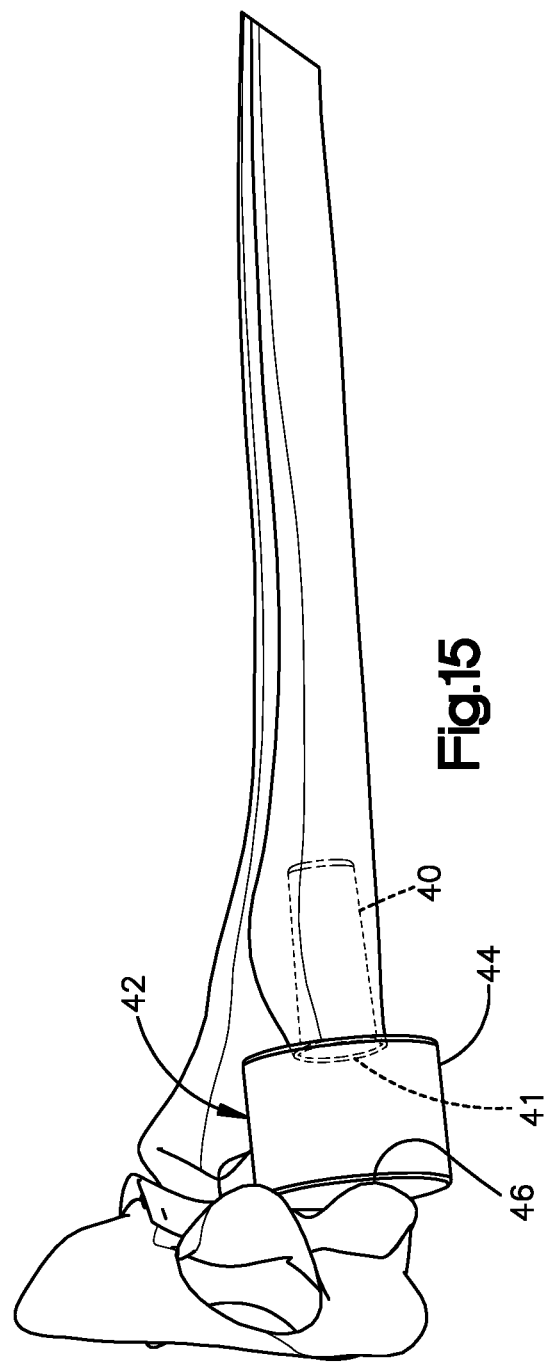

SURGICAL INSTRUMENT HANDLE WITH IMPLANT SIZING FEATURE AND METHOD OF USING

CROSS-REFERENCE TO RELATED APPLICATIONS

This is a divisional of U.S. patent application Ser. No. 16/560,923 filed Sep. 4, 2019, which is a continuation-in-part of U.S. patent application Ser. No. 16/245,191 filed Jan. 10, 2019 which, in turn, claims priority to U.S. Patent Application Ser. No. 62/638,240 filed Mar. 4, 2018, the disclosure if each of which is hereby incorporated by reference as if set forth in its entirety herein.

BACKGROUND

1. Technical Field

The present invention relates generally to orthopedic surgical instruments and, more particularly, to single use orthopedic surgical instruments.

2. Description of the Related Art

At present there exist many thousands of different hand-held surgical tools that are used for performing different procedures on the human or animal body. Typically, each tool has a functional tip that is integrally formed with a handle from metals such as cobalt chrome, stainless steel, or titanium.

Problems with tools of the type currently available include high material and manufacturing costs, as well as significant costs related to sterilizing such devices between surgeries. Disposable or Single use handles are one solution to these problems.

Accordingly, there is a need in the medical field for a disposable handle that may be used with a plurality of surgical devices.

Like other joints and anatomical features of the human body, the elbow joint is complex in its make-up and function. Also, like the other joints and anatomical features of the human body, the elbow joint is unique unto itself and requires specific consideration for its reconstruction or replacement. The complexity and uniqueness of this joint are best appreciated by considering the skeletal motions which are involved in its movement.

In the transition of the hand and forearm from pronation to supination the radius and ulna of the forearm transition from a crossed relationship to a side-by-side relationship. In this movement there is a relative rotation of the radius bone about the ulna. Also, during the transition between pronation and supination there is some relative translational movement between the radius bone and the ulna. The consequence of this is that from a reference point on the ulna, the radius bone appears to move with a general motion that includes both translation and rotation. The head of the radius interacts with the capitellum and the radial notch of the ulna during pronation and supination, providing elbow and forearm stability during rotation and translation.

In addition to its importance as a component of forearm function, the radial head is an equally important component of normal elbow function. Indeed, elbow function involves bending, lifting and twisting movements, all of which require joint stability. Because motions in the human body require the interaction of various anatomical components, it is important that replacement of a component be precise in form, size, and orientation. While the head of the radius bone directly engages the capitellum of the humerus and the radial notch of the ulna, it also relates indirectly to other anatomical components of the arm. Specifically, ligaments surrounding the radial head are essential to elbow stability. Further, misalignment of the radius bone will cause poor radial-capitellar joint contact, leading to subluxation, or poor alignment of the elbow. It follows that the wrist and shoulder joints are also affected by the alignment of the radius bone.

The importance of having a workable prosthesis for the head of the radius bone is underscored by the debilitating effects which commonly result when a joint becomes damaged due to fracture, arthritis, or osteochondrosis. It is well known that radial head resection, as seen in elbow injuries, results in persistent elbow instability. Additionally, forearm axial instability can result from radial head excision if the remaining stabilizers, i.e., the supporting ligaments, are compromised. Because this loss of stability affects the interdependent functions of the elbow and forearm, when the radial head is damaged, it is common to see further damage to other components of the radial-ulnar joint system, including, but not limited to, the complex system of supporting ligaments that encase the elbow joint. It has been well demonstrated that damage to any one of the components of the radial-ulnar joint system leads to pain, weakness, and loss of motion. It is, therefore, of great importance to the patient that damage to the radial head be remedied. As with all surgeries, it is desirable for such procedures to be performed as efficiently (quickly, safely, and accurately) as possible.

In current surgical techniques for radial head replacement, surgeons typically use the following steps: (1) performing an initial skin incision; (2) performing an extensor split; (3) resecting the radial neck; (4) reaming the canal; (5) planing the resected surface; (6) rebuilding the fragments in a sizer dish; (6) assembling the trial implant; (7) inserting the trial implant; (8) performing a trial range of motion; (9) removing the trial implant; (10) disassembling and reassembling the trial implant; (11) inserting the trial implant; (12) performing another trial range of motion; (13) removing the trial implant; and (14) inserting the final implant.

Referring now to FIGS. 1-3, there are shown various prior art radial head sizing devices. The sizing devices are typically configured as stand-alone trays having a plurality of openings of different known sizes. The resected bone from the radial neck is placed in at least one of the openings to determine the size of proximal radius. In particular, the resected bone can be placed in various ones of the openings until the resected bone is placed in an opening that substantially matches the size of the resected bone. Because the openings have known sizes, the size of the bone that matches one of the openings can be readily determined. The surgeon can then select a trial implant and final implant whose stem corresponds to the size of the resected bone.

Thus, a further need exists, for a device usable during humeral head replacement for a damaged elbow joint.

SUMMARY

In one example, an orthopedic handle is configured to removably attach to an orthopedic device. The handle can include a handle body having a connection end that is configured to connect the handle to the orthopedic device. The handle can further include a plurality of sizing cavities having different known maximum cross-sectional dimensions that each correspond to a size of an orthopedic implant.

The sizing cavities can be configured to receive resected bone so as to determine a size of the resected bone.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings:

FIG. 6 is a schematic top plan view of the instrument handle illustrated in FIG. 4:

FIG. 7 is a schematic bottom plan view of the instrument handle illustrated in FIG. 4.

FIG. 12A is a schematic exploded side elevation view of the instrument illustrated in FIG. 4, showing the working shaft aligned to be secured to the handle;

FIG. 12B is a schematic side elevation view of the instrument illustrated in FIG. 12A, showing the working shaft received in the handle;

FIG. 12C is a schematic side elevation view of the instrument illustrated in FIG. 12B, showing the working shaft secured to the handle;

FIG. 13A is a side elevation view of the working shaft as illustrated in FIG. 4, including a sounder having a first cross-sectional dimension;

FIG. 13B is a side elevation view of the working shaft as illustrated in FIG. 13A, including a sounder having a second cross-sectional dimension greater than the first cross-sectional dimension;

FIG. 13C is a side elevation view of the working shaft as illustrated in FIG. 13B, including a sounder having a third cross-sectional dimension greater than the second cross-sectional dimension;

FIG. 14A is a schematic side elevation view of a proximal radius having undergone a trauma;

FIG. 14B is a schematic side elevation view of the proximal radius illustrated in FIG. 14A, but showing a portion of the proximal radius resected to define a proximal edge;

FIG. 14C is a schematic side elevation view of the proximal radius illustrated in FIG. 14B, but showing the proximal edge planarized; and FIG. 15 shows a final radial implant that has been implanted in the proximal radius.

Corresponding reference characters indicate corresponding parts throughout the several views. The exemplary embodiments set forth herein are not to be construed as limiting the scope of the invention in any manner.

DETAILED DESCRIPTION

Figure 1:
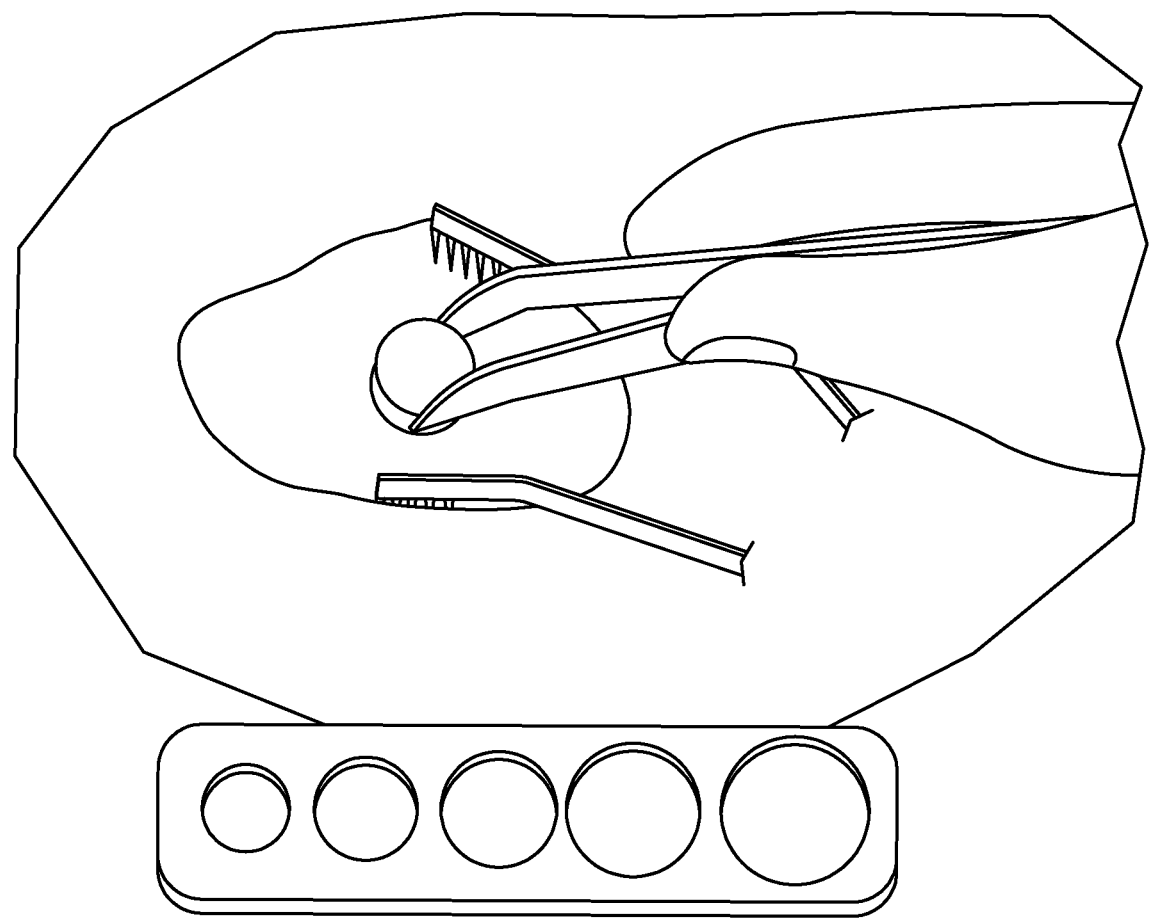
FIG. 1 shows prior art tray including a plurality of sizing cavities.
Figure 2:
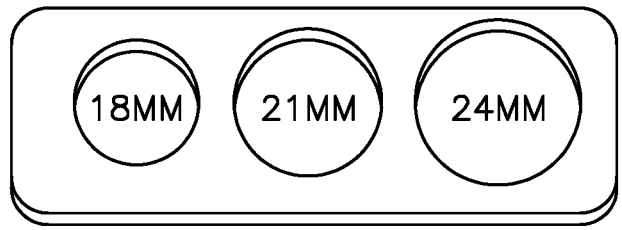
FIG. 2 shows a top view of another prior art tray including a plurality of sizing cavities.
Figure 3:
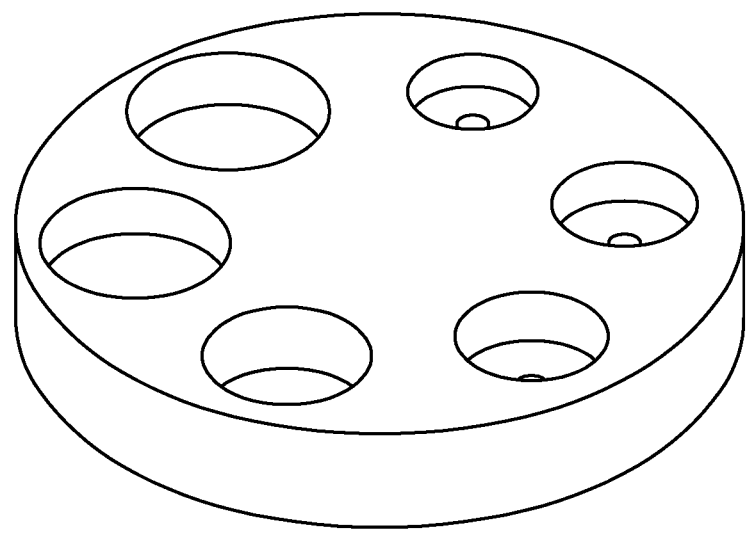
FIG. 3 is a perspective view of another prior art tray including a plurality of sizing cavities.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical". "horizontal", and derivatives thereof shall relate to the invention as oriented in the drawings.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Those of skill in the art will appreciate that prior art devices require various instrument sets to remove and reassemble the trial implant. Additionally, a surgeon must use a remote sizing device to determine the appropriate radial head implant size.

Figure 4:
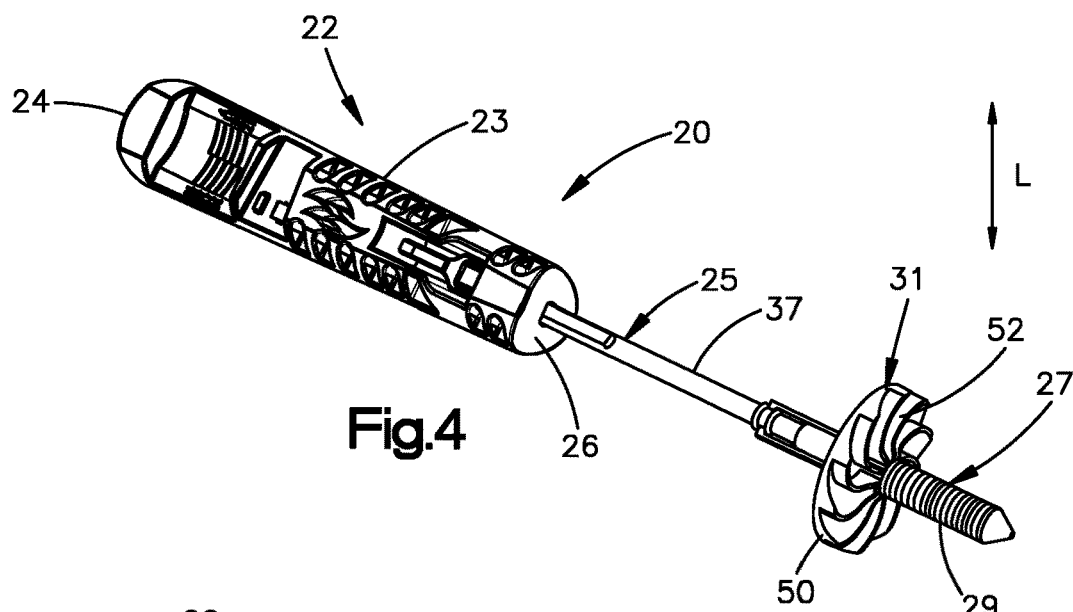
FIG. 4 is a perspective view of an instrument including a handle and a working shaft that extends from the handle.
Figure 5A:
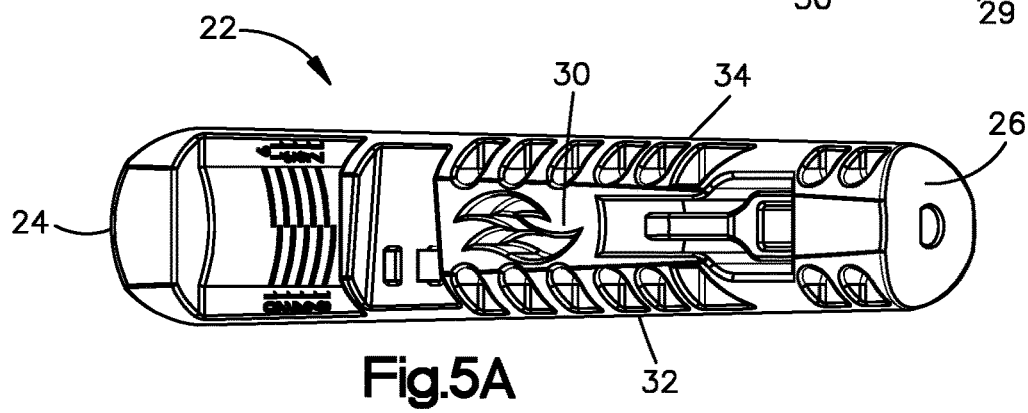
FIG. 5A is a perspective, view of the handle illustrated in FIG. 4, showing a bottom of the handle.
Figure 5B:
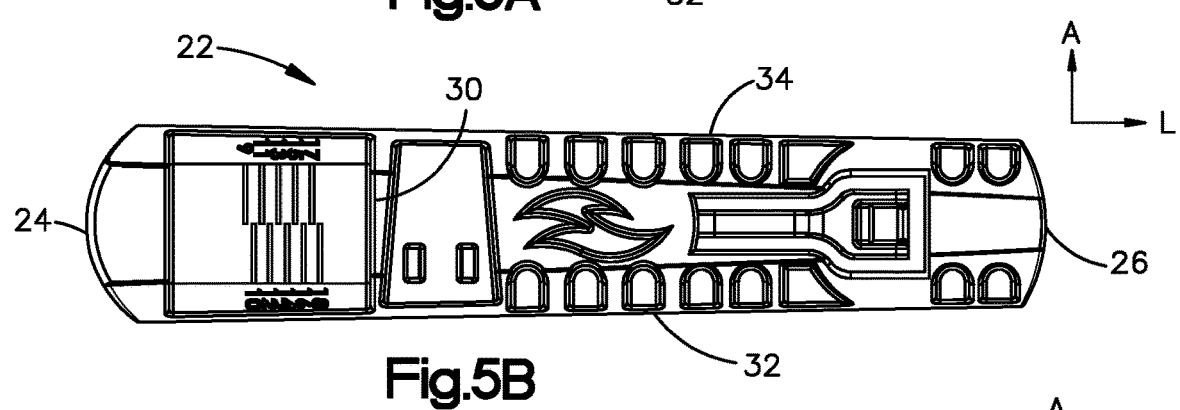
FIG. 5B is a bottom plan view of the handle illustrated in FIG. 5A.
Figure 5C:
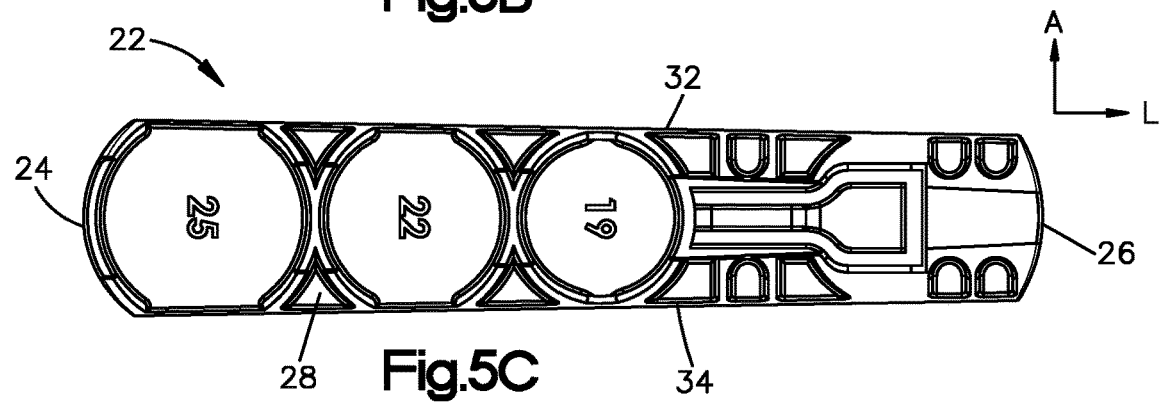
FIG. 5C is a top plan view of the handle illustrated in FIG. 5A.
Figure 5D:
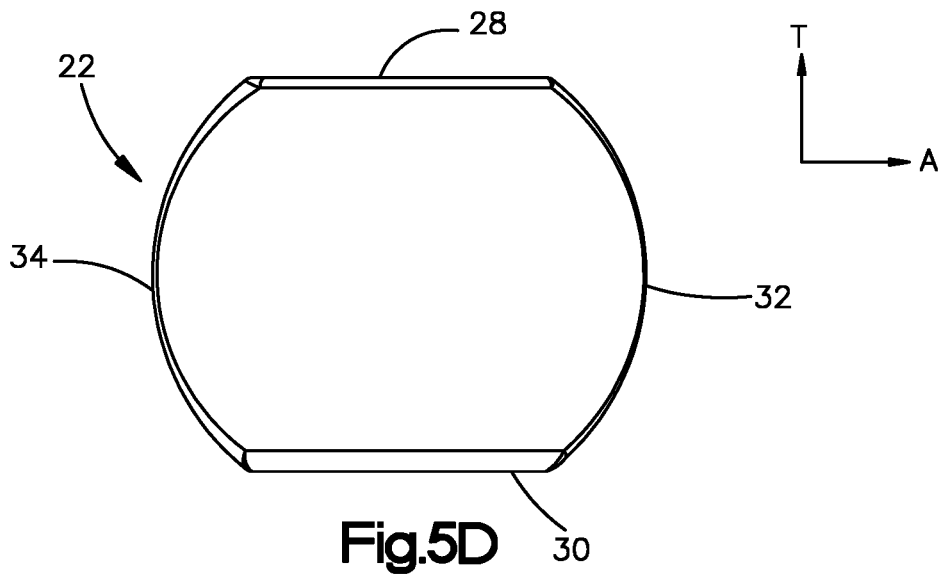
FIG. 5D is an end elevation view of a proximal end of the handle illustrated in FIG. 5A.
Figure 5E:
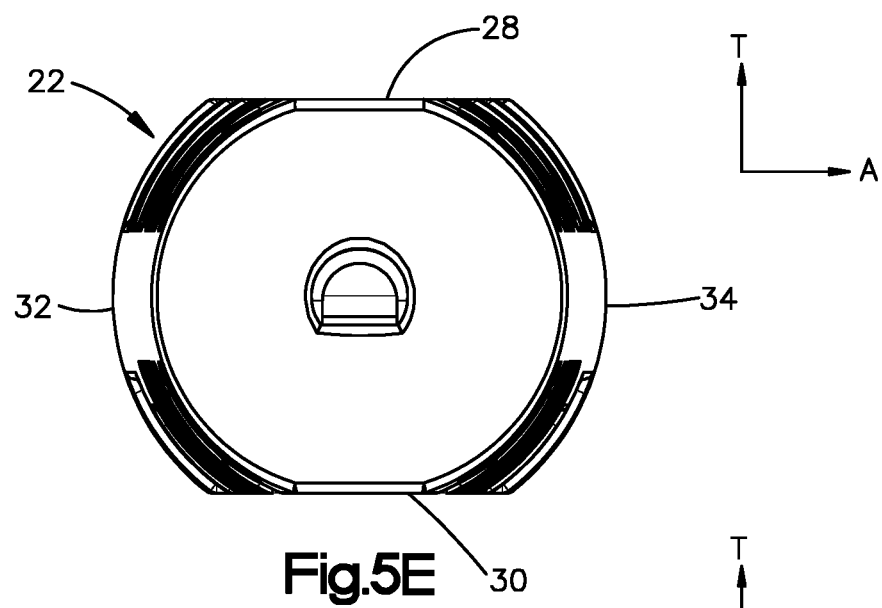
FIG. 5E is an end elevation view of a distal end of the handle illustrated in FIG. 5A.
Figure 5F:
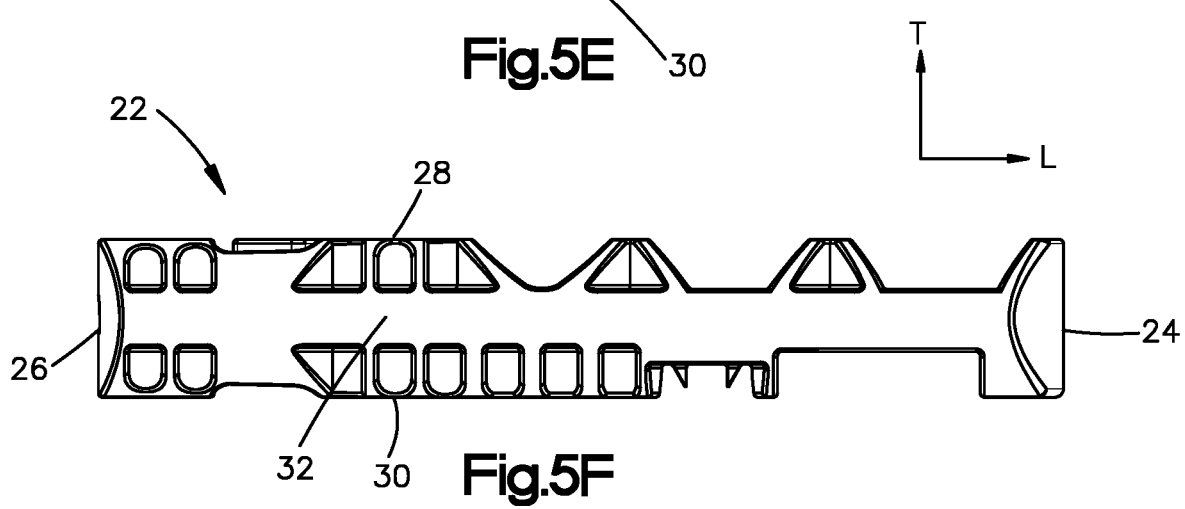
FIG. 5F is a side view of the handle illustrated in FIG. 5A, the opposed side view being a mirror image thereof.
Figure 8:
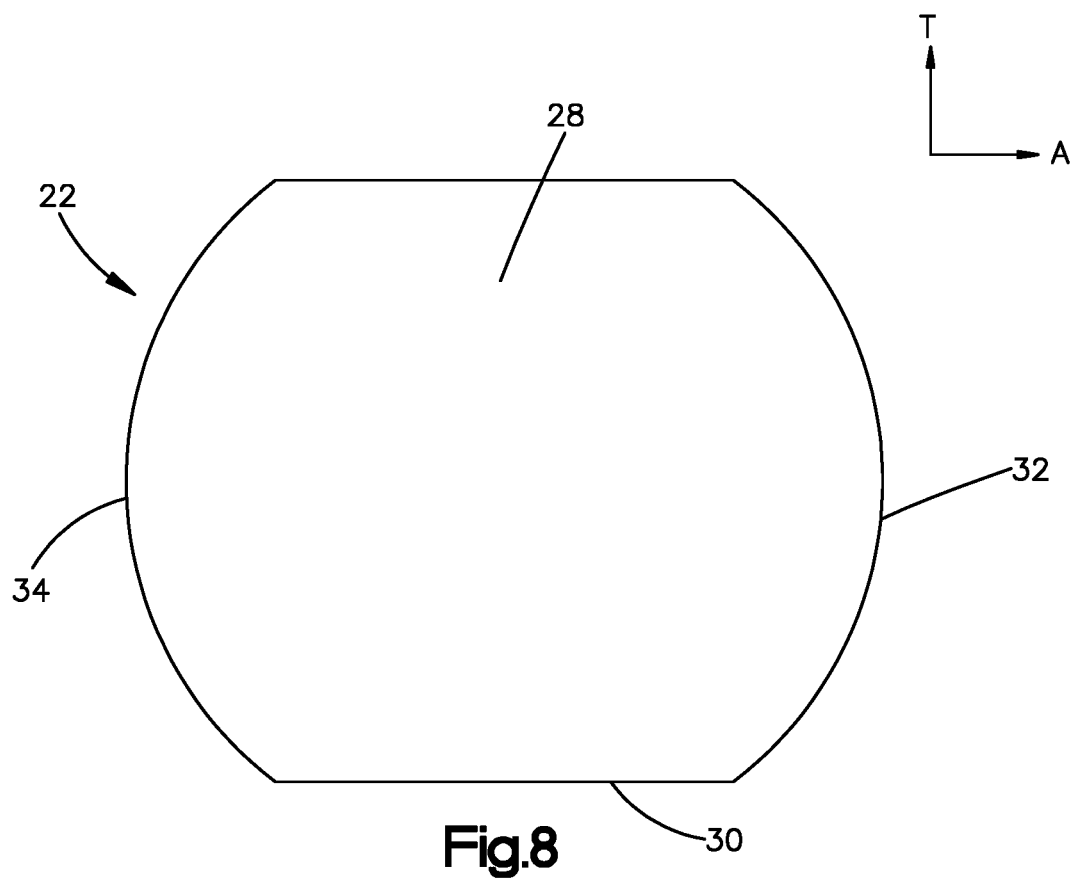
FIG. 8 is a schematic end elevation view of a proximal end of the instrument handle illustrated in FIG. 4.
Figure 9:
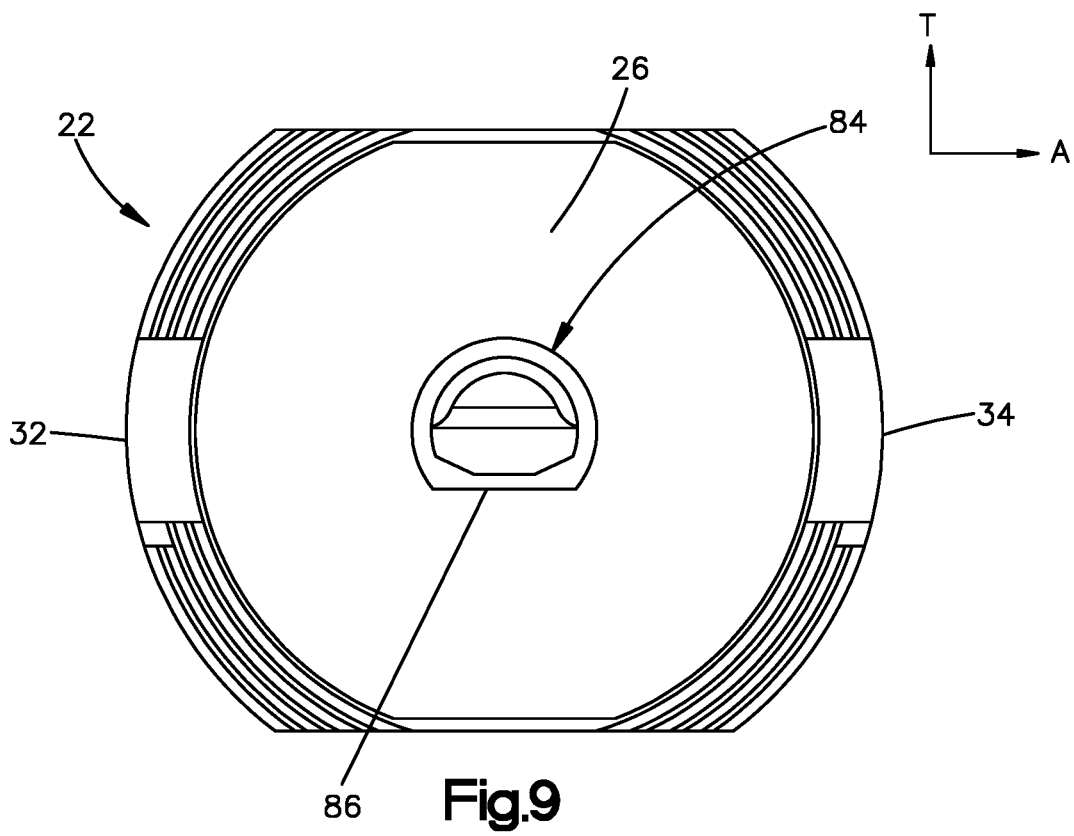
FIG. 9 is a schematic end elevation view of a distal end of the instrument handle illustrated in FIG. 4.

Referring now to FIG. 4, an orthopedic instrument 20 includes a handle 22 and an orthopedic device that can be configured as a working shaft 25 that can extend from the handle 22 along a distal direction. The instrument 20 is elongate along a longitudinal direction L that defines the distal direction, and extends along a central longitudinal axis 21. As will be described in more detail below, the shaft 25 can be removably attached to the handle 22. Further, the shaft 25 can include a shaft body 37 that, in turn, can define a working end 27. The working end 27 can support a sounder 29 that is configured to measure the diameter of the medullary canal of the proximal radius. The sounder 29 can be attached to the shaft body 37, or can be monolithic with the shaft body 37.

Referring now to FIGS. 13A-13C, a kit can include a plurality of shafts 25a-25c, respectively, that each includes a respective sounder 29a-29c, respectively, supported by the shaft body 37. A first sounder 29a of the plurality of sounders can define a first maximum cross-sectional dimension, which can be configured as a diameter. A second sounder 29b of the plurality of sounders can define a second maximum cross-sectional dimension, which can be configured as a diameter, that is greater than the first maximum cross-sectional dimension. A third sounder 29c of the plurality of sounders can define a third maximum cross-sectional dimension, which can be configured as a diameter, that is greater than the second maximum cross-sectional dimension. The shaft bodies 37 can be identical to each other, within manufacturing tolerances, at least to the extent that they are configured to attach selectively to the same handle 22. During operation, the sounders are driven into the medullary canal of the resected proximal radius until a select one of the sounders occupies a substantial entirety of the medullary canal. Each of the sounders 29 can define a respective plurality of ridges that project radially outward with respect to the shaft body 37 and can define the maximum cross-sectional dimension of the sounder.

Referring now to FIG. 15, the maximum cross-sectional dimension of the select one of the sounders corresponds to a maximum cross-sectional dimension, or diameter, of a stem 40 of a final radial implant 42. For instance, the stem 40 can be selected at the surgeon's discretion to be substantially equal to the maximum cross-sectional dimension of the select one of the sounders, or can be sized slightly less than the maximum cross-sectional dimension of the select one of the sounders. Thus, the stem 40 is sized to fit into the medullary canal. The stem 40 is then inserted into the medullary canal of the resected proximal radius 41. The radial implant 42 further includes a head 44 that extends from the stem 40 and defines an articular surface that is configured to articulate with a complementary articular surface 46 that is defined by one or both of the ulna and the humerus.

The maximum cross-sectional dimension of the select one of the sounders can also corresponds to a maximum cross-sectional dimension, or diameter, of a stem of a radial trial implant. That is, the stem of the radial trial implant can be selected at the surgeon's discretion to be substantially equal to the maximum cross-sectional dimension of the select one of the sounders, or can be sized slightly less than the maximum cross-sectional dimension of the select one of the sounders. Thus, the stem of the trial implant is sized to fit into the medullary canal. The radial trial implant can be implanted in the proximal radius to measure the height of the head of the trial implant along the longitudinal direction L. Once the head of the trial implant has the desired height, the trial implant can be removed, and the final radial implant 42 having the desired head height can be implanted in the proximal radius in the manner described above.

In this regard, it should be appreciated that a kit can be provided that includes at least one or both of a plurality of radial trial implants and a plurality of final radial implants 42. At least one of the trial implants can be differently sized from at least one other one of the trial implants. Similarly, at least one of the final radial implants can be differently sized from at least one other one of the final radial implants. For instance the kit can include radial trial implants with stems of different maximum cross-sectional dimensions to substantially correspond to the maximum cross-sectional dimension of the select one of the sounders based on the patient's anatomy. The kit can also include radial trial implants having heads of different heights along the longitudinal direction L to substantially span the longitudinal distance from the proximal radius to one or both of the ulna and the humerus based on the patient's anatomy. Further, the kit can include final radial implants with stems of different maximum cross-sectional dimensions to substantially correspond to the maximum cross-sectional dimension of the select one of the sounders based on the patient's anatomy. The kit can also include final radial implants having heads of different heights along the longitudinal direction L to substantially span the longitudinal distance from the proximal radius to one or both of the ulna and the humerus based on the patient's anatomy.

Referring now to FIG. 4, the working shaft 25 can further include a planarizer 31 that is supported by the shaft body 37. The planarizer 31 is configured to remove bone from a proximal edge 55 of the resected proximal radius so as to planarize the proximal edge so that a head of a radial implant can abut the substantially planar proximal edge. In particular, the planarizer 31 can define a body 50 having a plurality of teeth 52 that extend distally from a distal facing surface of the body 50. The teeth can define distal ends that can be substantially coplanar with each other. Further, the distal facing surface of the body 50 can be substantially planar. The teeth 52 can be curved or straight and linear as desired. Referring now to FIGS. 4 and 14A-14C, the proximal radius 51 has undergone a trauma that has caused one or more fractures 53, as shown in FIG. 14A. The fractured region of the proximal radius 51 can be removed, and a portion of the proximal radius can be resected as shown in FIG. 14B thereby defining the proximal edge 55. The planarizer 31 can be fixed to the shaft body 37 with respect to rotation, and the shaft 25 can be fixed to the handle 22 with respect to rotation. Thus, rotation of the handle 22 correspondingly rotates the planarizer 31, which causes the teeth 52 to remove bone from the proximal edge 55 and planarize the proximal edge 55 as shown in FIG. 14C. The head 44 of the final radial implant 42 (see FIG. 15) can rest against the planarized proximal edge.

Referring again to FIG. 4, it should be appreciated from the description above that the instrument 20 can be configured as a sounder for the proximal radius. Alternatively or additionally, the instrument 20 can further be configured as a planarizer that is configured to planarize the proximal radius.

Referring now to FIGS. 4-9 generally, the handle 22 includes a handle body 23 that, in turn, defines a first or proximal end 24 and a second or distal end 26 opposite the proximal end 24 along the longitudinal direction L. The proximal end 24 is opposite the distal end 26 along a proximal direction that can be defined substantially by the longitudinal direction L. Conversely, the distal end 26 is opposite the proximal end 24 along a distal direction that can be defined substantially by the longitudinal direction L. Thus, the term "distal," "distally," and derivatives thereof as used herein refer to a direction from the proximal end 24 to the distal end 26. The term "proximal," "proximal," and derivatives thereof as used herein refer to a direction from the distal end 26 to the proximal end 24.

The handle body 23, and thus the handle 22, has a top 28 and a bottom 30 that are opposite each other along a transverse direction T that is oriented substantially perpendicular to the longitudinal direction L. The handle body 23, and thus the handle 22, further defines first and second sides 32 and 34 that are opposite each other along a lateral direction A that is substantially perpendicular to each of the longitudinal direction L and the transverse direction T. In a plane that is defined by the transverse direction T and the lateral direction A, the top 28 and the bottom 30 define a width of the instrument handle 22 from the first side 32 to the second side 34. The first and second sides 32 and 34 define a thickness of the instrument handle 22 from the top 28 to the bottom 30. The width can be greater than the thickness. In one example, the first and second opposed sides 32 and 34 can taper toward each other as they extend in the distal direction. Alternatively, the first and second opposed sides 32 and 34 can extend substantially parallel to each other. Alternatively still, the first and second opposed sides 32 and 34 can taper toward each other as they extend in the proximal direction The term "substantially" and "approximate" and derivatives thereof as used herein recognizes that the referenced dimensions, sizes, shapes, directions, or other parameters can include the stated dimensions, sizes, shapes, directions, or other parameters and up to ±20%, including ±10%, ±5%, and ±2% of the stated dimensions, sizes, shapes, directions, or other parameters.

Referring now to FIG. 6 in particular, the handle 22 can include a plurality of sizing cavities 36 that are supported by the top 28 of the handle 22. The sizing cavities 36 can be defined by a respective at least one respective upwardly extending outer wall 38 that at least partially defines an outer perimeter of the sizing cavities 36. For instance, the top of the handle 22 can define a top surface 33, and the at least one outer wall 38 can extend out from the top surface 33. The at least one outer wall 38 can be configured as a single substantially cylindrical outer wall 38. The at least one outer wall 38 of each of the sizing cavities 36 can define an enclosed outer perimeter of the respective sizing cavities 36. Alternatively, the outer wall 38 of at least one or more of the sizing cavities 36 can define an open outer perimeter. In one example, the outer walls 38 can be monolithic with the handle body 23. For instance, the outer walls 38 can be defined by the top surface 33 of the handle 22. Alternatively, the outer walls 38 can be separate from the handle body 23 and attached to the handle body 23 as desired. The sizing cavities 36 can further include base upon which the resected bone can rest. The outer walls 38 can extend out with respect to the base.

Each of the sizing cavities 36 can define different cross-sectional dimensions as defined by the at least one outer wall 38. As described, the at least one outer wall can be a cylindrical outer wall 38. Thus, the cross-sectional dimensions can define respective diameters. In one example, the sizing cavities 36 can include a first sizing cavity 36a, a second sizing cavity 36b, and a third sizing cavity 36c. The first sizing cavity 36a can be sized smaller than the second sizing cavity 36b. The second sizing cavity 36b can be sized smaller than the third sizing cavity 36c. For instance, the first sizing cavity 36a can define a first cross-sectional dimension that is less than a second cross-sectional dimension of the second sizing cavity 36b. The second cross-sectional dimension of the second sizing cavity 36b can be less than a third cross-sectional dimension of the third sizing cavity 36c. The difference between the second cross-sectional dimension and the first cross-sectional dimension can be substantially equal to the difference between the third cross-sectional dimension and the second cross-sectional dimension. Alternatively, the difference between the second cross-sectional dimension and the first cross-sectional dimension can be different than the difference between the third cross-sectional dimension and the second cross-sectional dimension. In one nonlimiting example, the cross-sectional dimensions of the sizing cavities 36 can range from approximately 15 mm to approximately 30 mm, though other dimensions are envisioned.

The first sizing cavity 36a can be at least partially defined by a first outer wall 38a that at least partially defines a first outer perimeter of the first sizing cavity 36a. The second sizing cavity 36b can be at least partially defined by a second outer wall 38b that at least partially defines a second outer perimeter of the second sizing cavity 36b. The third sizing cavity 36c can be at least partially defined by a third outer wall 38c that at least partially defines a third outer perimeter of the third sizing cavity 36c. Respective centers of the sizing cavities 36 can be aligned with each other along the longitudinal direction L. Further, the respective centers of the sizing cavities 36 can lie on the central axis of the handle 22 with respect to a side elevation view of the handle 22 that includes the proximal end 24, the distal end 26, and the first and second opposed sides 32 and 34. Further, the second sizing cavity 36b can be disposed proximal of the first sizing cavity 36a. The third sizing cavity 36c can be disposed proximal of the second sizing cavity 36b. The third outer wall 38c can define the proximal end of the instrument handle 22 in some examples.

As described above, the first and second sides 32 and 34 can taper toward each other as they extend in the distal direction. Conversely, the first and second sides 32 and 34 can flare away from each other as they extend in the proximal direction. In one example, the first outer wall 38a can fully enclose the outer perimeter of first sizing cavity 36a. Thus, the diameter of the first sizing cavity 36a can be less than the width of the handle at a location aligned with the center of the first sizing cavity 36a. The second cross-sectional dimension of the second sizing cavity 36b can be greater than the width of the handle 22 at a location that intersects the respective center of the second sizing cavity 36b. Thus, the second outer perimeter of the second sizing cavity 36b can be open to at least one or both of the to the first and second sides 32 and 34. Accordingly, the second outer wall 38b can be defined by first and second outer wall segments spaced from each other along the longitudinal direction L. The first and second outer wall segments of the second outer wall 38b can be substantial mirror images of each other. The third cross-sectional dimension of the third sizing cavity 36c can be greater than the width of the handle 22 at a location that intersects the respective center of the third sizing cavity 36c. Thus, the third outer perimeter of the third sizing cavity 36c can be open to one or both of the first and second sides 32 and 34. Accordingly, the third outer wall 38c can be defined by first and second outer wall segments spaced from each other along the longitudinal direction L. The first and second outer wall segments of the third outer wall 38c can be substantial mirror images of each other. The outer wall segments of the third outer wall 38c can be longer than the outer wall segments of the second outer wall 38b. A greater extent of the third outer perimeter can be open to the first and second sides 32 and 34 with respect to the extent of the second outer perimeter that is open to the first and second sides.

Thus, is thus appreciated that at least one of the outer perimeters can be fully enclosed, and at least one other of the outer perimeters can be open to at least one or both of the first and second sides 32 and 34. Accordingly, one or more of the sizing cavities 36 can have a different size and shape with respect to one or more others of the sizing cavities 36. As will now be described, although the second and third outer perimeters can be open to the first and second sides 32 and 34, the respective second and third outer walls 38b and 38c, respectively, have a extend a sufficient distance to positively receive the resected bone 35 in the respective second and third sizing cavities 36b and 36c, respectively, when the size of the resected bone matches the size of the respective sizing cavity.

In particular, during operation, the resected bone 35 from the radial neck of the proximal radius can be placed in at least one of the sizing cavities 36 to determine the size of proximal radius. In particular, the resected bone 35 can be placed in a plurality of the sizing cavities 36 until the resected bone 35 is placed in a select sizing cavity 36 among the plurality of sizing cavities 36 that substantially matches the size of the resected bone 35. Thus, the select sizing cavity 36 can be identified as matching the size of the resected bone 35. As one example, the resected bone 35 can match the size of the second sizing cavity 36b. Because the cross-sectional dimensions of each of the sizing cavities 36 are known, the size of the bone 35 that matches the select one of the sizing cavities can be readily determined. The surgeon can then select for implantation into the proximal radius, selectively, an orthopedic implant that can be configured as one or both of a radial trial implant and a final radial implant having a head that has a maximum cross-sectional dimension or diameter that is substantially equal to or greater than that of the select one of the sizing cavities, at the surgeon's discretion. In this regard, the kit of at least one or both of a plurality of radial trial implants and a plurality of final radial implants can include heads of different cross-sectional dimensions or diameters that are substantially equal to the respective cross-sectional dimensions or diameters of the sizing cavities 36.

While the outer walls 38 have been described in one example, it is recognized that the outer walls 38 can define any suitable alternatively size and shape. For instance, the at least one outer wall 38 can be defined by a plurality of connected walls that at least partially define the outer perimeter of the sizing cavities 36. The outer perimeter of each of the sizing cavities can be an enclosed outer perimeter. Alternatively, at least a portion of the outer perimeter can be open. In another example, it is appreciated that the sizing cavities 36 can share one or more of the at least one outer wall 38. Further, while the handle 22 includes three differently sized sizing cavities 36 in one example, it is appreciated that the handle 22 can include any number of differently sized sizing cavities as desired, such as at least three.

Figure 10A:
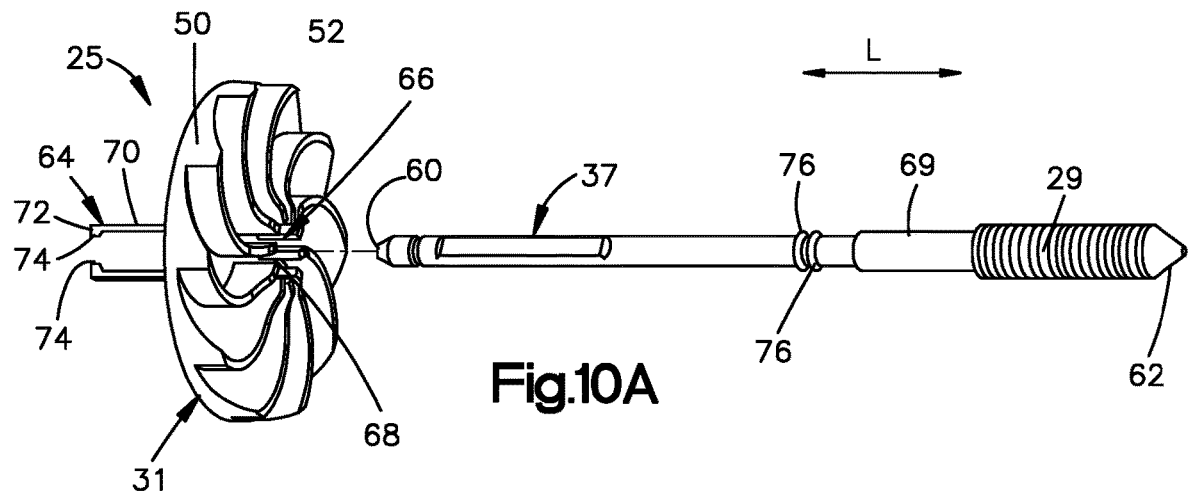
FIG. 10A is an exploded perspective view of a shaft body of the working shaft illustrated in FIG. 4 aligned to secure to a planarizer.
Figure 10B:
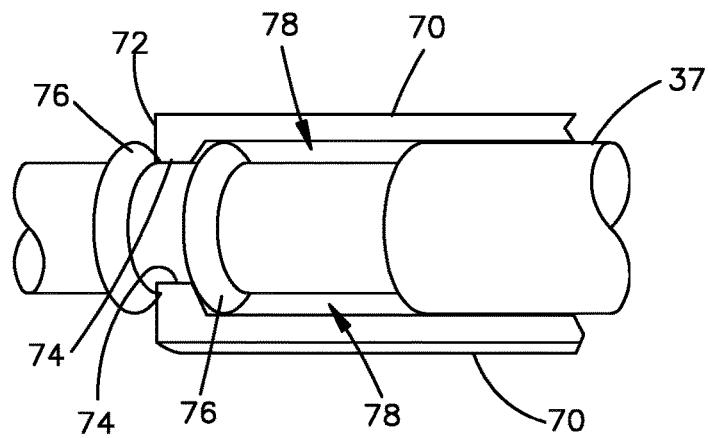
FIG. 10B is an enlarged side elevation view of the working shaft illustrated in FIG. 10A, showing the securement of the planarizer to the shaft body.
Figure 10C:
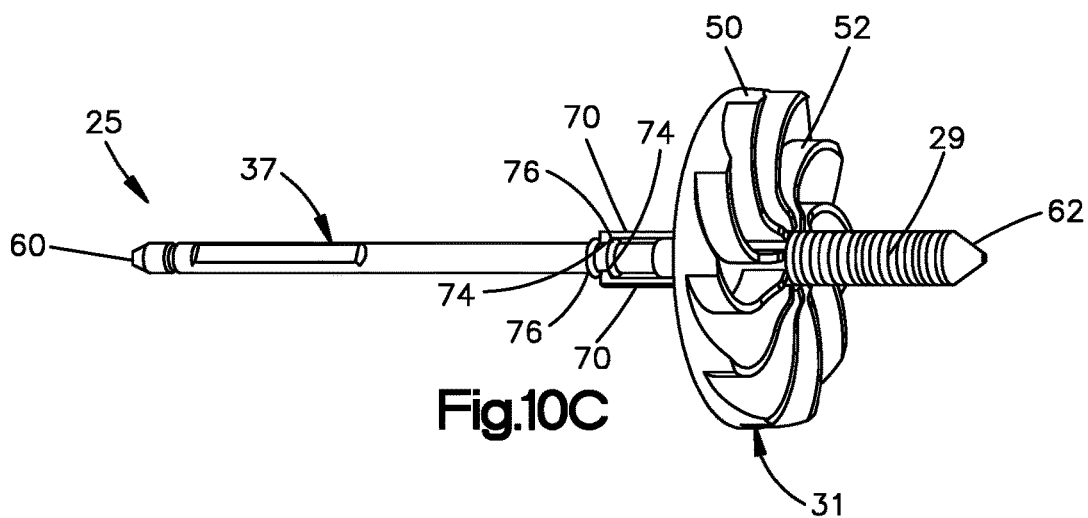
FIG. 10C is a side elevation view of the working shaft illustrated in FIG. 10A, showing the planarizer secured to the shaft body.

Referring now to FIGS. 10A-10C, the shaft body 37 defines a proximal end 60 and a distal end 62 opposite the proximal end 60 in the distal direction. The proximal end 60 is thus opposite the distal end 62 in the proximal direction. The distal end 62 can be defined by a working end 27 of the shaft body 37. As described above with respect to FIG. 4, the working shaft 25 can include the planarizer 31 that is configured to be supported by the shaft body 37 at the working end 27.

For instance, the planarizer 31 can define a central aperture 66 that extends centrally through the planarizer body 50 along the longitudinal direction L. The central aperture 66 can be keyed and thus configured to attach to the shaft body 37, which can also be keyed, so that the planarizer is rotatably coupled to the shaft body 37. For instance, the central aperture 66 can be partially defined by a flat surface 68, and the shaft can define a corresponding flat surface 69 that faces or abuts the flat surface 68. Therefore, when the shaft body 37 rotates about its central axis, the shaft body 37 similarly drives the planarizer 31 to rotate about its central axis.

Figure 11A:
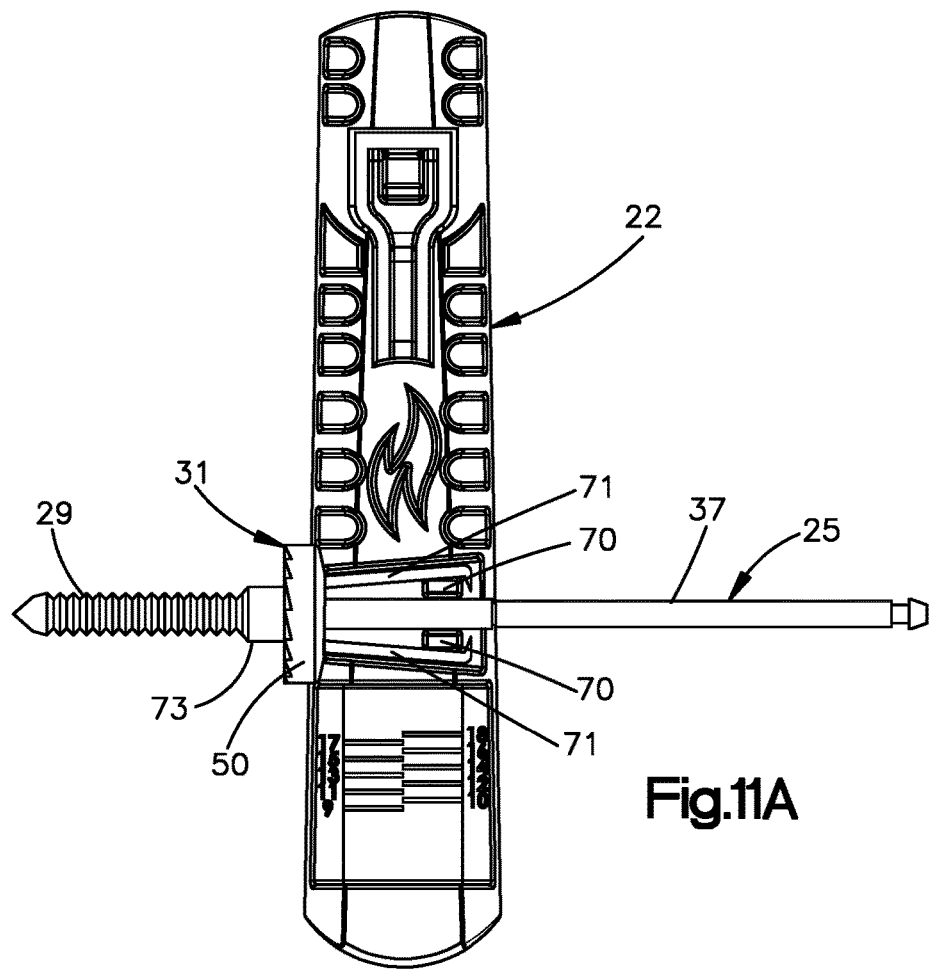
FIG. 11A is a schematic bottom plan view showing the working shaft aligned with the handle to decouple the planarizer from the shaft body.
Figures 11B, 11C:
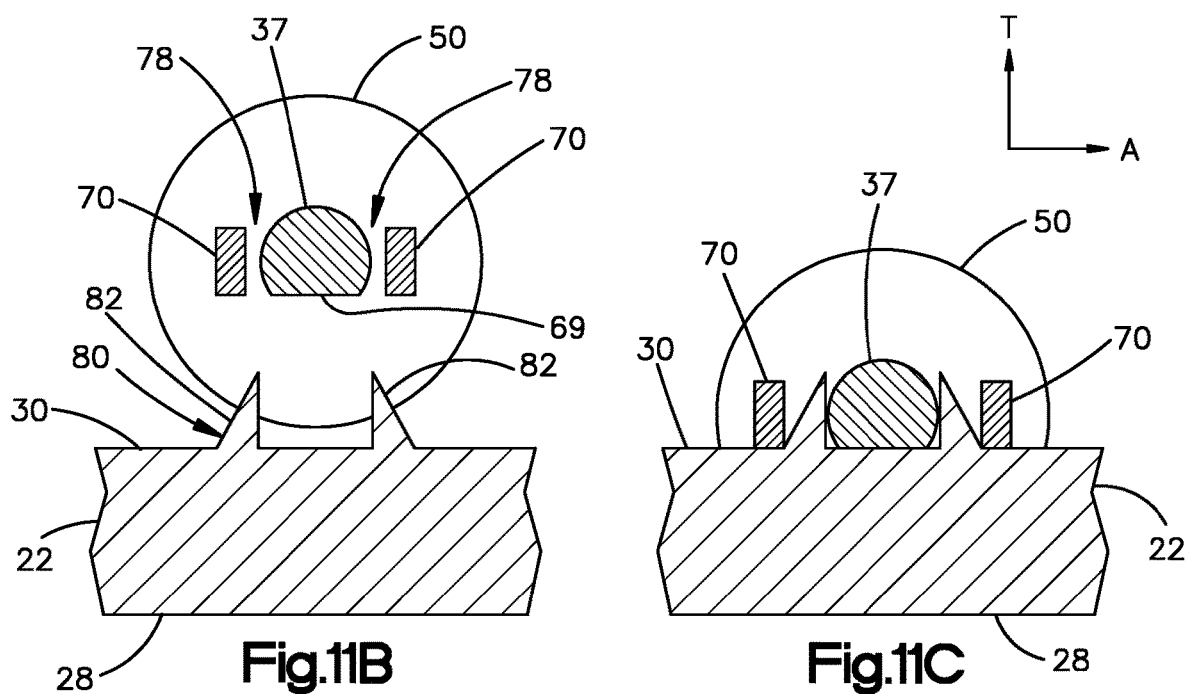
FIG. 11B is a schematic sectional side elevation view showing the working shaft aligned with the handle to decouple the planarizer from the shaft body as illustrated in FIG. 11A.
FIG. 11C is a schematic sectional side elevation view similar to FIG. 11B, but showing the planarizer decoupled from the shaft body.

The planarizer 31 defines an attachment member 64 that is configured to be coupled to the shaft body 37 so as to fix the planarizer 31 with respect to movement relative to the shaft body 37 along the longitudinal direction L. For instance, the planarizer can define at least one attachment arm 70 that is configured to couple the planarizer 31 to the shaft body 37. The at least one attachment arm 70 can extend proximally from a proximal-facing surface of the planarizer body 50 to a free end 72. The at least one attachment arm 70 can include an inwardly extending barb 74. The shaft 25 can further define a barb 76 that extends out from the shaft body 37. The planarizer 31 is translated distally along the shaft with the shaft body 37 received in the central aperture 66 until the barb 74 of the planarizer rides over the barb 76 of the shaft 25. Thus, the barb 74 of the planarizer 31 is disposed distal of the barb 76 of the shaft 25, and is in alignment with the barb 76 of the shaft 25. Thus, once the barb 74 of the planarizer 31 has moved to a position distal of the barb 76 of the shaft 25 as shown in FIGS. 10B-10C, the barb 76 of the shaft interferes with the barb 74 of the planarizer 31 to limit or prevent movement of the planarizer 31 in the distal direction along the shaft body 37. The planarizer body 50 can also abut a distal facing shoulder of the shaft body 37 along the longitudinal direction L. Thus, the distal facing surface of a shoulder 73 (see FIG. 11A) and the barb 76 of the shaft body 37 capture the planarizer 31 with respect to movement relative to the shaft body 37 along the longitudinal direction L.

In one example, the planarizer 31 can define first and second opposed attachment arms 70 that are each configured to couple to the shaft body 37. The barb 74 of each of the attachment arms 70 can project inwardly toward the other one of the arms 70. The barbs 74 can flare distally as they extend inward. Similarly, the at least one barb 76 of the shaft can include first and second barbs 76. The barbs 74 are configured to ride over the barbs 76 to couple the planarizer 31 to the shaft body 37 in the manner described above.

Referring now to FIGS. 10B-10C and 11A-11C, it is recognized that it may be desirable to remove the planarizer 31 from the shaft body 37. For instance, if the sounder 29 is not properly sized in the medullary canal of the proximal radius, it may be desirable to couple the planarizer 31 a shaft body 37 that supports a properly sized sounder 29. The working shaft 25 can define first and second gaps 78 that extend from the shaft body 37 to the first and second arms 70, respectively. The handle 22 can include an ejector 80 that is configured to decouple the planarizer 31 from the shaft body 37. For instance, the ejector is configured to be inserted into the gap 78 to urge the arms outward away from the shaft body 37, thereby removing the barbs 74 of the planarizer 31 from interference with the barbs 76 of the shaft body 37 along the longitudinal direction. Thus, the planarizer 31 can be translated relative to the shaft body 37 along the proximal direction, thereby removing the planarizer 31 from the shaft 25.

The ejector 80 can be configured as a wedge member having at least one ramped surface 82 that flares laterally inward as it extends out from an outer surface the handle 22 along the transverse direction T to a free end. The outer surface can be defined by the bottom surface 30 of the handle 22 in some examples. It should be appreciated, however, that the ejector 80 can be alternatively positioned as desired. The free ends of the ramped surfaces 82 can be aligned with the gap 78 along a removal direction of the shaft 25 with respect to the handle 22. The removal direction can be toward the handle. Further, the removal direction can be defined substantially by the transverse direction T. Next, the working shaft 25 is translated along the removal direction, which inserts the ramped surface 82 into the gap 78. The ramped surfaces 82 can ride along either or both of the attachment arms 70 and the shaft body 37. In one example, the ramped surface 82 can ride along the attachment arms 70, thereby urging the arms 70 outward away from each other, and away from the shaft body 37. The working shaft 25 can be moved in the removal direction until the shaft body 37 contacts the handle 22. The working shaft 25 can be oriented such that its central axis is oriented along the lateral direction A, or perpendicular to the central axis of the handle 22. In this regard, the ramped surfaces 82 can be spaced from each other substantially along the lateral direction A.

The arms 70 are urged away from the shaft body 37 until the barbs 74 and 76 are no longer in longitudinal alignment with each other. In this regard, it can be desirable to move the shaft body 37 toward or against the handle 22 when the shaft body 37 is oriented such that the flat surface 69 faces or abuts the handle 22. Moving the shaft body 37 toward or against the handle 22 can cause the attachment arms 70 to be positioned as close as possible to the outer surface of the handle 22, and thus provides the maximum movement of the attachment arms 70 away from the shaft body 37. The handle 22 can define abutment surfaces 71 that flare away from each other as they extend in the proximal direction relative to the shaft body 37. Thus, the attachment arms 70 can abut the abutment surfaces 71 when they have been moved fully away from each other. Next, the planarizer can be removed from the shaft body by moving the planarizer 31 along the proximal direction relative to the shaft body 37. This can be achieved by moving the planarizer 31 in the proximal direction with respect to the shaft body 37, by moving the shaft body 37 in the distal direction with respect to the planarizer 31, or both.

While one method and apparatus from removing the planarizer 31 from the shaft body 37 has been described, it should be appreciated that any suitable alternative method and apparatus for applying a force to the arms that moves the arms 70 away from the shaft body 37 to correspondingly remove the interference between the barbs 74 and 76 is envisioned.

Referring now to FIGS. 4 and 12A-12C, the working shaft 25 can be attached to the handle 22. Further, the working shaft 25 can be rotationally locked to the handle 22, such that rotation of the handle 22 causes the working shaft 25 to similarly rotate. In one example, the planarizer 31 can be coupled to the shaft body 37 before the working shaft 25 is attached to the handle 22. The handle 22 can include a receiving aperture 84 that extends through the distal end 26 along the longitudinal direction L. The receiving aperture 84 can be keyed in the manner as described above with respect to the central aperture 66 of the planarizer 31. Thus, the receiving aperture 84 can be configured to receive the shaft body 37, which can also be keyed, so that the shaft body 37 is rotatably coupled to the handle 22. In this regard, the handle body 23 can prevent rotation of the shaft 25 about a longitudinal axis. For instance, the receiving aperture 84 can be partially defined by a flat surface 86, and the shaft body 37 can define a corresponding flat surface that faces or abuts the flat surface 86. Therefore, when the handle 22 rotates about its central axis, the shaft body 37 similarly rotates about its central axis. Thus, the distal end 26 can be referred to as a connection end that is configured to connect to the shaft 25.

The working shaft 25 is further configured to be attached to the handle 22, which fixes the working shaft 25 with respect to movement of the working shaft 22 along the longitudinal direction L relative to the handle 22. In particular, the handle 22 can include an actuator 88 is supported by the handle body 23. The actuator 88 can have an actuator surface 90 and an engagement member 92. The actuator 88 can be resiliently supported in an initial or neutral position. Thus, a biasing force urges the actuator 88 toward its neutral position when the actuator 88 is moved from the neutral position. The actuator surface 90 can extend out with respect to an outer surface of the handle 22. In one example, the actuator surface 90 can extend out with respect to the top surface 28. It should be appreciated, of course, that the actuator surface 90 can be positioned at any alternative location as desired.

The engagement member 92 of the handle 22 can be configured to mate with a corresponding engagement member 94 of the working shaft 25. For instance, the engagement member 92 of the handle can be configured as a projection 93 that extends out along a direction substantially perpendicular to the longitudinal direction L. The engagement member 94 of the working shaft 25 can be configured as a recess 95 that is configured to receive the projection 93 so as to attach the shaft 25 to the handle 22 and lock the shaft 25 with respect to translation relative to the handle 22 along the longitudinal direction L. Alternatively, the engagement member 92 of the handle 22 can be configured as a recess, and the engagement member 94 of the working shaft 25 can be configured as a projection that is received in the recess.

The working shaft 25 can be inserted into the handle 22 in the proximal direction until the engagement member 94 of the shaft 25 is aligned with the engagement member 92 of the actuator 88. The handle 22 can include a stop wall 96 that is aligned with the proximal end 60 of the shaft 25 along the proximal direction. The engagement members 92 and 95 can be aligned with each other when the shaft 25 contacts the stop wall 96. The stop surface 95 prevents further movement of the shaft 25 along the proximal direction when the shaft 25 contacts the stop wall 96. The actuator shaft 25 can be said to be in a fully inserted position when the engagement member 94 of the shaft 25 is aligned with the engagement member 92 of the actuator 88.

As the shaft 25 is inserted into the handle 22 to its fully inserted position, the projection 92 can ride along the outer surface of the shaft body 37, which deflects the actuator 88 from its initial or neutral position to a deflected position. The actuator 88 is biased to return to its neutral position, which urges the projection 92 against the shaft body 37. When the shaft 25 engagement members 92 and 94 are aligned with each other, the projection 92 is biased to move into the recess 95 of the shaft 25, thereby mating the engagement members 92 and 94 and locking the shaft 25 to the handle 22. Thus, the actuator 88 can be said to be in its locked position when the engagement members 92 and 94 are mated to each other, as illustrated in FIG. 12C. Because the actuator 88 is biased to return to its neutral position, the engagement member 92 of the actuator 88 is biased into engagement with the engagement member 94 of the shaft 25.

In one example, the actuator 88 can further include a blocking wall 98 that is configured to prevent full insertion of the shaft 25 into the handle 22 to its fully inserted position when the actuator 88 is in its neutral position. In particular, the blocking wall 98 can be aligned with the proximal end 60 of the shaft 25 when the actuator 88 is in its neutral position. Accordingly, when the shaft 25 is moved in the proximal direction into or through the aperture 84, the shaft abuts the blocking wall 98, which prevents the shaft 25 from moving further in the proximal direction to its fully inserted position. A force can be applied to the actuator 88 that moves the actuator from its neutral position past the deflected position to an interference removal position shown in FIG. 12B that, in turn, moves the blocking wall 98 out of alignment with the shaft 25. In particular, the engagement surface 90 can be depressed to remove the blocking wall 98 from alignment with the shaft 25. In this regard, the actuator 88 can be referred to as a button.

When the actuator 88 is maintained in the interference removal position, the shaft 25 can be inserted into the handle 22 to its fully inserted position. Removal of the applied force causes the actuator 88 to resiliently move to its locked position, which causes the engagement members 92 and 94 to mate with each other in the manner described above.

The shaft 25 can be removed from the handle 22 by applying an unlocking force to the actuator 88 that moves the actuator from the locked position further away from the neutral position, which unmates the engagement members 92 and 94 from each other. In particular, the projection 93 is removed from the recess 95. Removal of the unlocking force allows the biasing force to return the actuator 88 to its neutral position.

Advantageously, a single handle 22 can include the sizing cavities 36 (see FIG. 6) and can also attach to the working shaft 25 that can include one or both of a sounder 29 and a planarizer 31 (see FIGS. 4 and 12C).

Referring again to FIG. 4, when the shaft 25 is attached to the handle 22, the sounder 29 of the shaft 25 can be inserted into the medullary canal of the proximal radius. If the sounder 29 does not match the size of the medullary canal, the shaft 25 can be removed from the handle 22 in the manner described above. The planarizer 31 can then be removed from the shaft body 37 in the manner described above. The planarizer 31 can then be coupled to another shaft body 37 having a differently sized sounder 29. Once the shaft body 37 has been selected having the desired sounder 29 that fits into the medullary canal and contacts cortical bone, the planarizer 31 can planarize the proximal edge of the proximal radius by rotating the handle about its central longitudinal axis, thereby rotating the planarizer 31 in the manner as described above. It is appreciated that the handle 22 can be manually rotated about its central longitudinal axis so as to correspondingly rotate the planarizer 31 and planarize the proximal edge of the proximal radius. It is recognized, of course, that in instances whereby the sounder 29 is too small but still fits into the medullary canal, the planarizer of the shaft 25 can planarize the proximal edge of the proximal radius. Thus, the planarizer 31 would not need to be attached to the shaft having the differently sized sounder 29. In other examples, the surgeon may elect not to planarize the proximal radius, in which case the planarizer 31 would not need to be attached to the shaft 25. Thus, the shaft 25 can support the sounder 29 but not the planarizer 31.

Advantageously, the handle 22 can be constructed as a single-use handle. Thus, the handle 22 can have a melting point below 249 degrees Fahrenheit in one example. As a result, in this example, the structural integrity of the handle 22 would be compromised when subjected to temperatures of at least 249 degrees Fahrenheit for at least 30 minutes by using saturated steam under at least 15 psi of pressure, as is common in a sterilizing autoclave. In one example, an entirety of the handle can be any suitable polymer, which allows the handle 22 to be manufactured inexpensively as a single-use handle. The handle 22 can be made from any suitable biocompatible and disposable material. For instance, the handle 22 can be made of any suitable recyclable material in some examples.

It should be noted that the illustrations and discussions of the embodiments shown in the figures are for exemplary purposes only and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

What is claimed:

1. A method comprising the steps of:
attaching a working shaft to a handle, wherein the working shaft includes a shaft body and a sounder supported by the shaft body;
resecting a proximal radius to define a resected bone;
inserting the resected bone into a plurality of sizing cavities of the handle until the resected bone is placed in a select sizing cavity among the plurality of sizing cavities that matches a size of the resected bone; and
selecting an implant for a proximal radius having a head that corresponds to the size of the resected bone.

2. The method of claim 1, wherein the size of the resected bone comprises a maximum cross-sectional dimension.

3. The method of claim 2, wherein the head is substantially equal to or greater than the size of the resected bone.

4. The method of claim 1, wherein the attaching step comprises inserting the shaft into an aperture of the handle, wherein the aperture and the shaft body are keyed to rotatably fix the shaft with respect to the handle.

5. The method of claim 4, further comprising the step of locking the shaft in a fully inserted position.

6. The method of claim 5, wherein the locking step comprises mating an engagement member of the handle with an engagement member of the shaft.

7. The method of claim 6, wherein the locking step comprises moving a resilient actuator from a neutral position to a locked position.

8. The method of claim 7, further comprising the step of moving the actuator to a position whereby a blocking wall is moved from a position that interferes with the insertion of the shaft to a position out of interference with the insertion of the shaft.

9. The method of claim 1, wherein the handle comprises a material having a melting point less than 249 degrees Fahrenheit.

10. The method of claim 1, further comprising the step of decoupling a planarizer from the shaft body that also supports a sounder.

\* \* \* \* \*